US009875574B2

(12) United States Patent
Bendall

(10) Patent No.: US 9,875,574 B2
(45) Date of Patent: Jan. 23, 2018

(54) METHOD AND DEVICE FOR AUTOMATICALLY IDENTIFYING THE DEEPEST POINT ON THE SURFACE OF AN ANOMALY

(71) Applicant: General Electric Company, Schenectady, NY (US)

(72) Inventor: Clark Alexander Bendall, Syracuse, NY (US)

(73) Assignee: General Electric Company, Schenectady, NY (US)

(*) Notice: Subject to any disclaimer, the term of this patent is extended or adjusted under 35 U.S.C. 154(b) by 971 days.

(21) Appl. No.: 14/108,976

(22) Filed: Dec. 17, 2013

(65) Prior Publication Data

US 2015/0170352 A1 Jun. 18, 2015

(51) Int. Cl.
*G06T 17/00* (2006.01)
*G01B 11/22* (2006.01)
(Continued)

(52) U.S. Cl.
CPC .............. *G06T 17/00* (2013.01); *G01B 11/22* (2013.01); *G01N 21/8851* (2013.01);
(Continued)

(58) Field of Classification Search
CPC ....... G06T 17/00; G06T 7/001; G06T 7/0012; G06T 7/0051; G06T 7/0063; G06T 7/0067; G06T 2207/10028; G06T 2207/20112; G06T 2207/20096; G01B 11/24; G01B 11/30; G01B 13/22; G01N 21/8851;
(Continued)

(56) References Cited

U.S. PATENT DOCUMENTS 3,657,638 A * 4/1972 Holler .................... G01N 27/83
324/213
4,188,122 A * 2/1980 Massie ..................... G01J 9/04
356/489

(Continued)

FOREIGN PATENT DOCUMENTS

CN 1158684 A 9/1997
EP 00549182 A2 6/1993
(Continued)

OTHER PUBLICATIONS

Yerex et al. "Predictive Display Models for Tele-Manipulation from Uncalibrated Camera-Capture of Scene Geometry and Appearance", IEEE 2003.

(Continued)

*Primary Examiner* — Manav Seth
(74) *Attorney, Agent, or Firm* — Barclay Damon LLP

(57) ABSTRACT

A method and device for automatically identifying the deepest point on the surface of an anomaly on a viewed object using a video inspection device. The video inspection device obtains and displays an image of the surface of the viewed object. A reference surface is determined along with a region of interest that includes a plurality of points on the surface of the anomaly. The video inspection device determines a depth for each of the plurality of points on the surface of the anomaly in the region of interest. The point on the surface of the anomaly having the greatest depth is identified as the deepest point.

18 Claims, 7 Drawing Sheets

(51) Int. Cl.
*G01N 21/88* (2006.01)
*G06F 3/0484* (2013.01)
*G06T 7/00* (2017.01)
*H04N 13/00* (2006.01)

(52) U.S. Cl.
CPC ...... *G06F 3/04842* (2013.01); *G06F 3/04847* (2013.01); *G06T 7/001* (2013.01); *G01N 2021/8861* (2013.01); *G01N 2021/8887* (2013.01); *G06T 2207/10028* (2013.01); *H04N 2013/0081* (2013.01)

(58) Field of Classification Search
CPC ......... G01N 2201/08; G01N 2201/102; G06K 9/00214; G06K 2209/19
See application file for complete search history.

(56) References Cited

U.S. PATENT DOCUMENTS

| | | | | |
|---|---|---|---|---|
| 4,357,660 A * | | 11/1982 | Hepp | G01V 3/20 324/323 |
| 4,493,105 A | | 1/1985 | Beall et al. | |
| 4,688,184 A * | | 8/1987 | Taniguti | G01B 11/24 356/614 |
| 4,980,763 A | | 12/1990 | Lia | |
| 4,983,836 A * | | 1/1991 | Matoba | G01N 25/72 250/330 |
| 4,988,886 A | | 1/1991 | Palum et al. | |
| 5,066,119 A | | 11/1991 | Bertrand | |
| 5,175,601 A | | 12/1992 | Fitts | |
| 5,198,877 A * | | 3/1993 | Schulz | G01B 11/24 356/141.4 |
| 5,273,429 A * | | 12/1993 | Rekow | A61C 13/0004 433/215 |
| 5,302,999 A | | 4/1994 | Oshida et al. | |
| 5,307,152 A | | 4/1994 | Boehnlein et al. | |
| 5,434,669 A | | 7/1995 | Tabata et al. | |
| 5,510,833 A | | 4/1996 | Webb et al. | |
| 5,581,352 A | | 12/1996 | Zeien | |
| 5,607,607 A * | | 3/1997 | Naiman | A61F 2/02 219/121.61 |
| 5,633,675 A | | 5/1997 | Danna et al. | |
| 5,810,719 A | | 9/1998 | Toida | |
| 5,822,066 A | | 10/1998 | Jeong et al. | |
| 6,011,624 A | | 1/2000 | de Groot | |
| 6,064,759 A | | 5/2000 | Buckley et al. | |
| 6,083,162 A | | 7/2000 | Vining | |
| 6,201,541 B1 | | 3/2001 | Shalom et al. | |
| 6,299,309 B1 * | | 10/2001 | Ruiz | A61F 9/008 351/212 |
| 6,323,952 B1 | | 11/2001 | Yomoto et al. | |
| 6,438,272 B1 | | 8/2002 | Huang et al. | |
| 6,459,481 B1 | | 10/2002 | Schaack | |
| 6,670,962 B2 | | 12/2003 | Perry et al. | |
| 6,674,891 B1 * | | 1/2004 | Sameshima | G01B 11/24 382/152 |
| 6,717,578 B1 | | 4/2004 | Deering | |
| 6,909,988 B2 * | | 6/2005 | Batzinger | B21O 51/00 451/5 |
| 6,945,931 B2 | | 9/2005 | Ogawa | |
| 6,956,576 B1 | | 10/2005 | Deering et al. | |
| 7,030,996 B2 | | 4/2006 | De Groot et al. | |
| 7,170,677 B1 | | 1/2007 | Bendall et al. | |
| 7,286,246 B2 | | 10/2007 | Yoshida | |
| 7,298,499 B2 * | | 11/2007 | Fournier | G01B 11/25 356/237.1 |
| 7,372,558 B2 * | | 5/2008 | Kaufman | G03B 31/00 356/237.2 |
| 7,388,679 B2 | | 6/2008 | Yoshino et al. | |
| 7,453,456 B2 | | 11/2008 | Petrov et al. | |
| 7,474,803 B2 * | | 1/2009 | Petrov | G06K 9/20 345/419 |
| 7,486,805 B2 | | 2/2009 | Krattiger | |
| 7,518,632 B2 | | 4/2009 | Konomura | |
| 7,551,293 B2 | | 6/2009 | Yelin et al. | |
| 7,570,363 B2 | | 8/2009 | Takahashi | |
| 7,570,370 B2 | | 8/2009 | Steinbichler et al. | |
| 7,755,817 B2 | | 7/2010 | Ho et al. | |
| 7,782,453 B2 | | 8/2010 | Bendall et al. | |
| 7,812,968 B2 | | 10/2010 | Bendall et al. | |
| 7,821,649 B2 | | 10/2010 | Bendall et al. | |
| 7,855,732 B2 | | 12/2010 | Williams et al. | |
| 7,899,598 B2 | | 3/2011 | Woon et al. | |
| 8,165,351 B2 | | 4/2012 | Bendall | |
| 8,265,425 B2 * | | 9/2012 | Ng-Thow-Hing | G06T 7/0042 382/199 |
| 8,300,920 B2 | | 10/2012 | Chang et al. | |
| 8,422,030 B2 | | 4/2013 | Bendall et al. | |
| 8,443,704 B2 * | | 5/2013 | Burke | B23C 3/30 82/1.11 |
| 8,512,918 B2 * | | 8/2013 | Shoki | B82Y 10/00 430/22 |
| 8,582,207 B2 * | | 11/2013 | Fukuda | C08J 7/047 349/112 |
| 8,686,943 B1 * | | 4/2014 | Rafii | G06F 3/017 345/158 |
| 8,760,447 B2 * | | 6/2014 | Bendall | G06T 7/0004 345/419 |
| 8,810,636 B2 | | 8/2014 | Bendall | |
| 8,849,620 B2 * | | 9/2014 | Regan | G06F 17/50 345/419 |
| 9,013,469 B2 * | | 4/2015 | Bendall | G01B 11/24 345/419 |
| 2001/0018644 A1 | | 8/2001 | Schwalb et al. | |
| 2002/0163573 A1 | | 11/2002 | Bieman et al. | |
| 2004/0189799 A1 | | 9/2004 | Spencer | |
| 2006/0150124 A1 | | 7/2006 | Hornegger et al. | |
| 2006/0282009 A1 | | 12/2006 | Oberg et al. | |
| 2007/0206204 A1 | | 9/2007 | Jia et al. | |
| 2008/0198159 A1 | | 8/2008 | Liu et al. | |
| 2009/0059242 A1 | | 3/2009 | Fujieda et al. | |
| 2009/0158315 A1 | | 6/2009 | Bendall et al. | |
| 2009/0225321 A1 | | 9/2009 | Bendall et al. | |
| 2009/0225329 A1 | | 9/2009 | Bendall et al. | |
| 2009/0225333 A1 | | 9/2009 | Bendall et al. | |
| 2010/0284607 A1 | | 11/2010 | Van Den Hengel et al. | |
| 2011/0115730 A1 * | | 5/2011 | Kim | G06F 3/04883 345/173 |
| 2011/0115791 A1 * | | 5/2011 | Sabiston | A61F 2/5046 345/419 |
| 2011/0187824 A1 | | 8/2011 | Hori | |
| 2011/0210961 A1 * | | 9/2011 | Bendall | G06T 7/0004 345/419 |
| 2011/0221877 A1 * | | 9/2011 | Hori | H04N 7/183 348/65 |
| 2011/0260033 A1 * | | 10/2011 | Steffensen | G01C 15/002 250/203.1 |
| 2012/0069012 A1 | | 3/2012 | Facchin et al. | |
| 2012/0223937 A1 * | | 9/2012 | Bendall | G01B 11/24 345/419 |
| 2012/0256901 A1 | | 10/2012 | Bendall | |
| 2012/0314058 A1 | | 12/2012 | Bendall et al. | |
| 2013/0287288 A1 * | | 10/2013 | Bendall | G06T 7/0004 382/154 |
| 2014/0005978 A1 * | | 1/2014 | Shimizu | G01B 21/20 702/167 |
| 2015/0170412 A1 * | | 6/2015 | Bendall | G06T 17/00 382/119 |
| 2015/0196202 A1 * | | 7/2015 | Mercader | A61B 18/00 600/478 |
| 2015/0339817 A1 * | | 11/2015 | Kuriyama | G06T 1/0007 348/71 |
| 2016/0155015 A1 * | | 6/2016 | Bendall | G06T 7/001 382/199 |
| 2016/0171705 A1 * | | 6/2016 | Bendall | G01B 11/03 382/103 |
| 2016/0196643 A1 * | | 7/2016 | Bendall | G06T 7/0008 382/108 |

(56) References Cited

U.S. PATENT DOCUMENTS

FOREIGN PATENT DOCUMENTS

| EP | 00888522 A1 | 1/1999 |
| GB | 2328280 A | 2/1999 |
| GB | 2505926 A | 3/2014 |
| JP | 11213177 A | 8/1999 |
| JP | 2001149319 A | 6/2001 |
| JP | 2005331488 A | 12/2005 |
| JP | 2007029460 A | 2/2007 |
| JP | 3898945 B2 | 3/2007 |
| JP | 2009053147 A | 3/2009 |
| WO | WO-2006056614 A1 | 6/2006 |
| WO | WO-2010107434 A1 | 9/2010 |

OTHER PUBLICATIONS

Cobzas et al. "A Panoramic Model for Remote Robot Environment Mapping and Predictive Display", Published 2005.

Search Report and Written Opinion from EP Application No. 12157924.7 dated Jun. 22, 2012.

Miniaturized three-dimensional endoscopic imaging system based on active stereovision Authors: Manhong Chan; Wumei Lin; Changhe Zhou; Qu Jianan Y, Name and Date: Applied Optics ISSN 003-6935 Coden Apopai, 2003, vol. 42, n10, pp. 1888-1898 (11 page article).

Unofficial English translation of Office Action and Search Report issued in connection with related CN Application No. 201210063764.6 dated Sep. 2, 2015.

Unofficial English translation of Office Action issued in connection with related JP Application No. 2012044901 dated Feb. 2, 1996.

Unofficial English translation of Office Action and Search Report issued in connection with related CN Application No. 201210063764.6 dated Apr. 18, 2016.

International Search Report and Written Opinion issued in connection with related Application No. PCT/US2016/022312 dated Jul. 5, 2016.

Unofficial English translation of Japanese Office Action issued in connection with related JP Application No. 2012-044901 dated Feb. 2, 2016.

Unofficial English translation of Chinese Office Action and Search Report issued in connection with related CN Application No. 201210063764.6 dated Apr. 18, 2016.

\* cited by examiner

METHOD AND DEVICE FOR AUTOMATICALLY IDENTIFYING THE DEEPEST POINT ON THE SURFACE OF AN ANOMALY

BACKGROUND OF THE INVENTION

The subject matter disclosed herein relates to a method and device for automatically identifying the deepest point on the surface of an anomaly on a viewed object using a video inspection device.

Video inspection devices, such as video endoscopes or borescopes, can be used to inspect a surface of an object to identify and analyze anomalies (e.g., pits or dents) on the object that may have resulted from, e.g., damage, wear, corrosion, or improper installation. In many instances, the surface of the object is inaccessible and cannot be viewed without the use of the video inspection device. For example, a video inspection device can be used to inspect the surface of a blade of a turbine engine on an aircraft or power generation unit to identify any anomalies that may have formed on the surface to determine if any repair or further maintenance is required. In order to make that assessment, it is often necessary to obtain highly accurate dimensional measurements of the surface and the anomaly to verify that the anomaly does not exceed or fall outside an operational limit or required specification for that object.

A video inspection device can be used to obtain and display a two-dimensional image of the surface of a viewed object showing the anomaly to determine the dimensions of an anomaly on the surface. This two-dimensional image of the surface can be used to generate three-dimensional data of the surface that provides the three-dimensional coordinates (e.g., (x, y, z)) of a plurality of points on the surface, including proximate to an anomaly. In some video inspection devices, the user can operate the video inspection device in a measurement mode to enter a measurement screen in which the user places cursors on the two-dimensional image to determine geometric dimensions of the anomaly. In many instances, the contour of a viewed feature is difficult to assess from the two-dimensional image, making highly accurate placement of the cursors proximate to the anomaly difficult. For example, when trying to measure the depth of an anomaly, it may be difficult to determine from the two-dimensional image the location of, and place a cursor on, the deepest point on the surface of the anomaly.

In some video inspection devices, the depth of an anomaly is determined by placing three cursors one at a time around the anomaly to establish a reference plane and then a fourth cursor at a point not on the plane to determine the perpendicular distance between the reference surface and the surface at the fourth point. This depth measurement is most often used to try to measure the deepest point on the surface of the anomaly. After each cursor is positioned using a joystick, the user presses a button to indicate that they are done with that cursor and are ready for the next, after which a new cursor is arbitrarily initially positioned at the center of the screen. Accordingly, for the fourth cursor of a depth measurement, the user has to move the cursor from the center of the screen to the location of the anomaly, and then must move the cursor around to find the deepest point on the surface of the anomaly manually. This process can be time consuming and may not always result in the deepest point being identified.

The discussion above is merely provided for general background information and is not intended to be used as an aid in determining the scope of the claimed subject matter.

BRIEF DESCRIPTION OF THE INVENTION

A method and device for automatically identifying the deepest point on the surface of an anomaly on a viewed object using a video inspection device is disclosed. The video inspection device obtains and displays an image of the surface of the viewed object. A reference surface is determined along with a region of interest that includes a plurality of points on the surface of the anomaly. The video inspection device determines a depth for each of the plurality of points on the surface of the anomaly in the region of interest. The point on the surface of the anomaly having the greatest depth is identified as the deepest point. An advantage that may be realized in the practice of some disclosed embodiments of the method and device for automatically identifying the deepest point on the surface of an anomaly is that the time to perform the depth measurement is reduced and the accuracy of the measurement is improved since the user does not need to manually identify the deepest point.

In one embodiment, a method of automatically identifying a deepest point on a surface of an anomaly on a surface of a viewed object. The method comprises the steps of obtaining an image of the surface of the viewed object with an imager, displaying on a monitor an image of the viewed object, determining the three-dimensional coordinates of a plurality of points on the surface of the viewed object using a central processor unit, determining a reference surface using the central processor unit, determining a region of interest that includes a plurality of points on the surface of the anomaly using a central processor unit, determining a depth for each of the plurality of points on the surface of the anomaly in the region of interest using a central processor unit, and determining the point on the surface of the anomaly in the region of interest having the greatest depth as the deepest point on the surface of the anomaly using a central processor unit.

In another embodiment, a device for automatically identifying a deepest point on a surface of an anomaly on a surface of a viewed object. The device comprises an imager for obtaining an image of the surface of the viewed object, a monitor for displaying an image of the viewed object, and a central processor unit for determining the three-dimensional coordinates of a plurality of points on the surface of the viewed object, determining a reference surface, determining a region of interest that includes a plurality of points on the surface of the anomaly, determining a depth for each of the plurality of points on the surface of the anomaly in the region of interest, and determining the point on the surface of the anomaly in the region of interest having the greatest depth as the deepest point on the surface of the anomaly.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
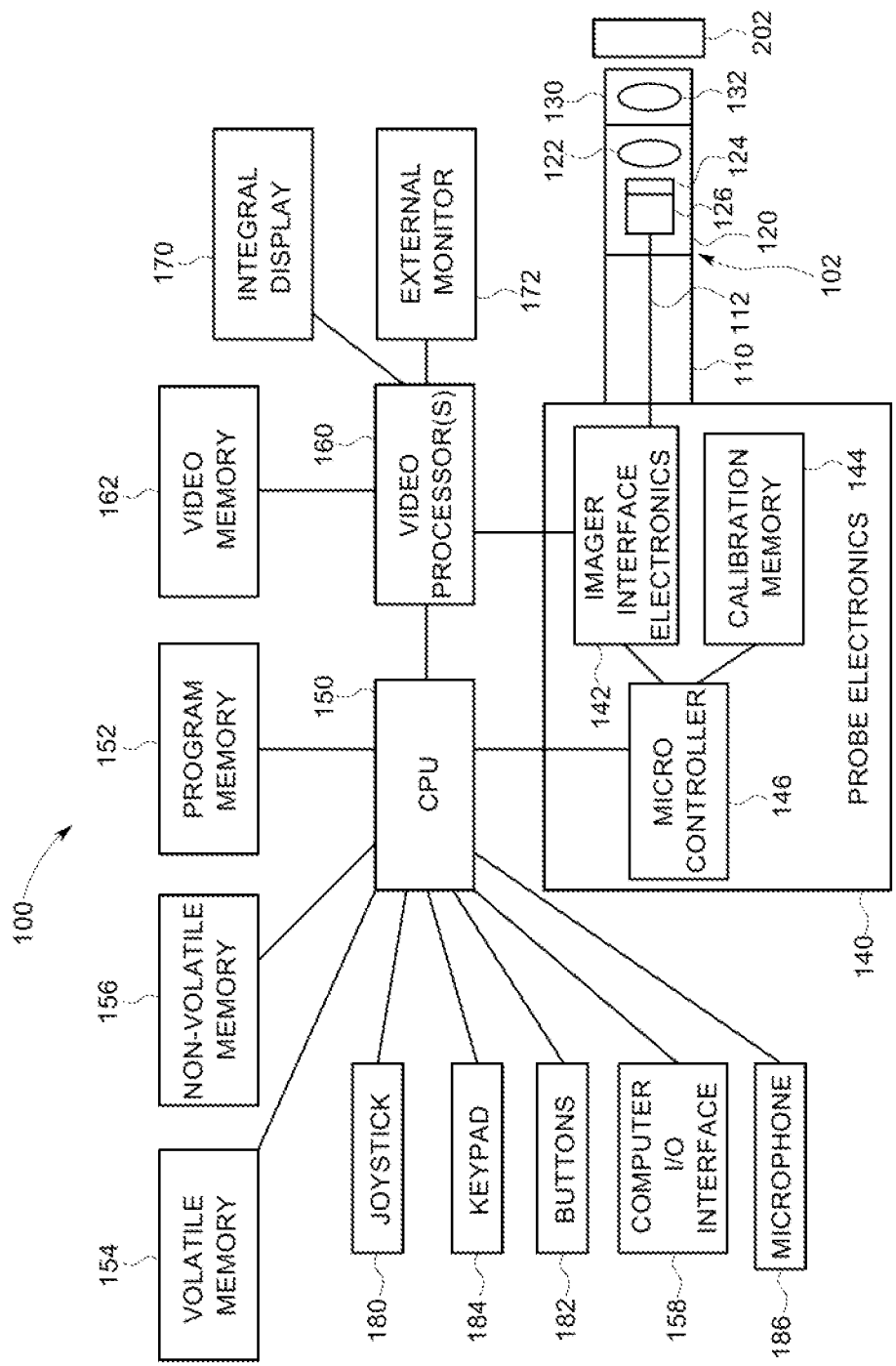
FIG. 1 is a block diagram of an exemplary video inspection device.

FIG. 1 is a block diagram of an exemplary video inspection device 100. It will be understood that the video inspection device 100 shown in FIG. 1 is exemplary and that the scope of the invention is not limited to any particular video inspection device 100 or any particular configuration of components within a video inspection device 100.

Video inspection device 100 can include an elongated probe 102 comprising an insertion tube 110 and a head assembly 120 disposed at the distal end of the insertion tube 110. Insertion tube 110 can be a flexible, tubular section through which all interconnects between the head assembly 120 and probe electronics 140 are passed. Head assembly 120 can include probe optics 122 for guiding and focusing light from the viewed object 202 onto an imager 124. The probe optics 122 can comprise, e.g., a lens singlet or a lens having multiple components. The imager 124 can be a solid state CCD or CMOS image sensor for obtaining an image of the viewed object 202.

A detachable tip or adaptor 130 can be placed on the distal end of the head assembly 120. The detachable tip 130 can include tip viewing optics 132 (e.g., lenses, windows, or apertures) that work in conjunction with the probe optics 122 to guide and focus light from the viewed object 202 onto an imager 124. The detachable tip 130 can also include illumination LEDs (not shown) if the source of light for the video inspection device 100 emanates from the tip 130 or a light passing element (not shown) for passing light from the probe 102 to the viewed object 202. The tip 130 can also provide the ability for side viewing by including a waveguide (e.g., a prism) to turn the camera view and light output to the side. The tip 130 may also provide stereoscopic optics or structured-light projecting elements for use in determining three-dimensional data of the viewed surface. The elements that can be included in the tip 130 can also be included in the probe 102 itself.

The imager 124 can include a plurality of pixels formed in a plurality of rows and columns and can generate image signals in the form of analog voltages representative of light incident on each pixel of the imager 124. The image signals can be propagated through imager hybrid 126, which provides electronics for signal buffering and conditioning, to an imager harness 112, which provides wires for control and video signals between the imager hybrid 126 and the imager interface electronics 142. The imager interface electronics 142 can include power supplies, a timing generator for generating imager clock signals, an analog front end for digitizing the imager video output signal, and a digital signal processor for processing the digitized imager video data into a more useful video format.

The imager interface electronics 142 are part of the probe electronics 140, which provide a collection of functions for operating the video inspection device 10. The probe electronics 140 can also include a calibration memory 144, which stores the calibration data for the probe 102 and/or tip 130. A microcontroller 146 can also be included in the probe electronics 140 for communicating with the imager interface electronics 142 to determine and set gain and exposure settings, storing and reading calibration data from the calibration memory 144, controlling the light delivered to the viewed object 202, and communicating with a central processor unit (CPU) 150 of the video inspection device 100.

In addition to communicating with the microcontroller 146, the imager interface electronics 142 can also communicate with one or more video processors 160. The video processor 160 can receive a video signal from the imager interface electronics 142 and output signals to various monitors 170, 172, including an integral display 170 or an external monitor 172. The integral display 170 can be an LCD screen built into the video inspection device 100 for displaying various images or data (e.g., the image of the viewed object 202, menus, cursors, measurement results) to an inspector. The external monitor 172 can be a video monitor or computer-type monitor connected to the video inspection device 100 for displaying various images or data.

The video processor 160 can provide/receive commands, status information, streaming video, still video images, and graphical overlays to/from the CPU 150 and may be comprised of FPGAs, DSPs, or other processing elements which provide functions such as image capture, image enhancement, graphical overlay merging, distortion correction, frame averaging, scaling, digital zooming, overlaying, merging, flipping, motion detection, and video format conversion and compression.

The CPU 150 can be used to manage the user interface by receiving input via a joystick 180, buttons 182, keypad 184, and/or microphone 186, in addition to providing a host of other functions, including image, video, and audio storage and recall functions, system control, and measurement processing. The joystick 180 can be manipulated by the user to perform such operations as menu selection, cursor movement, slider adjustment, and articulation control of the probe 102, and may include a push-button function. The buttons 182 and/or keypad 184 also can be used for menu selection and providing user commands to the CPU 150 (e.g., freezing or saving a still image). The microphone 186 can be used by the inspector to provide voice instructions to freeze or save a still image.

The video processor 160 can also communicate with video memory 162, which is used by the video processor 160 for frame buffering and temporary holding of data during processing. The CPU 150 can also communicate with CPU program memory 152 for storage of programs executed by the CPU 150. In addition, the CPU 150 can be in communication with volatile memory 154 (e.g., RAM), and non-volatile memory 156 (e.g., flash memory device, a hard drive, a DVD, or an EPROM memory device). The non-volatile memory 156 is the primary storage for streaming video and still images.

The CPU 150 can also be in communication with a computer I/O interface 158, which provides various interfaces to peripheral devices and networks, such as USB, Firewire, Ethernet, audio I/O, and wireless transceivers. This computer I/O interface 158 can be used to save, recall, transmit, and/or receive still images, streaming video, or audio. For example, a USB "thumb drive" or CompactFlash memory card can be plugged into computer I/O interface 158. In addition, the video inspection device 100 can be configured to send frames of image data or streaming video data to an external computer or server. The video inspection device 100 can incorporate a TCP/IP communication protocol suite and can be incorporated in a wide area network including a plurality of local and remote computers, each of the computers also incorporating a TCP/IP communication protocol suite. With incorporation of TCP/IP protocol suite, the video inspection device 100 incorporates several transport layer protocols including TCP and UDP and several different layer protocols including HTTP and FTP.

It will be understood that, while certain components have been shown as a single component (e.g., CPU 150) in FIG. 1, multiple separate components can be used to perform the functions of the component.

Figure 2:
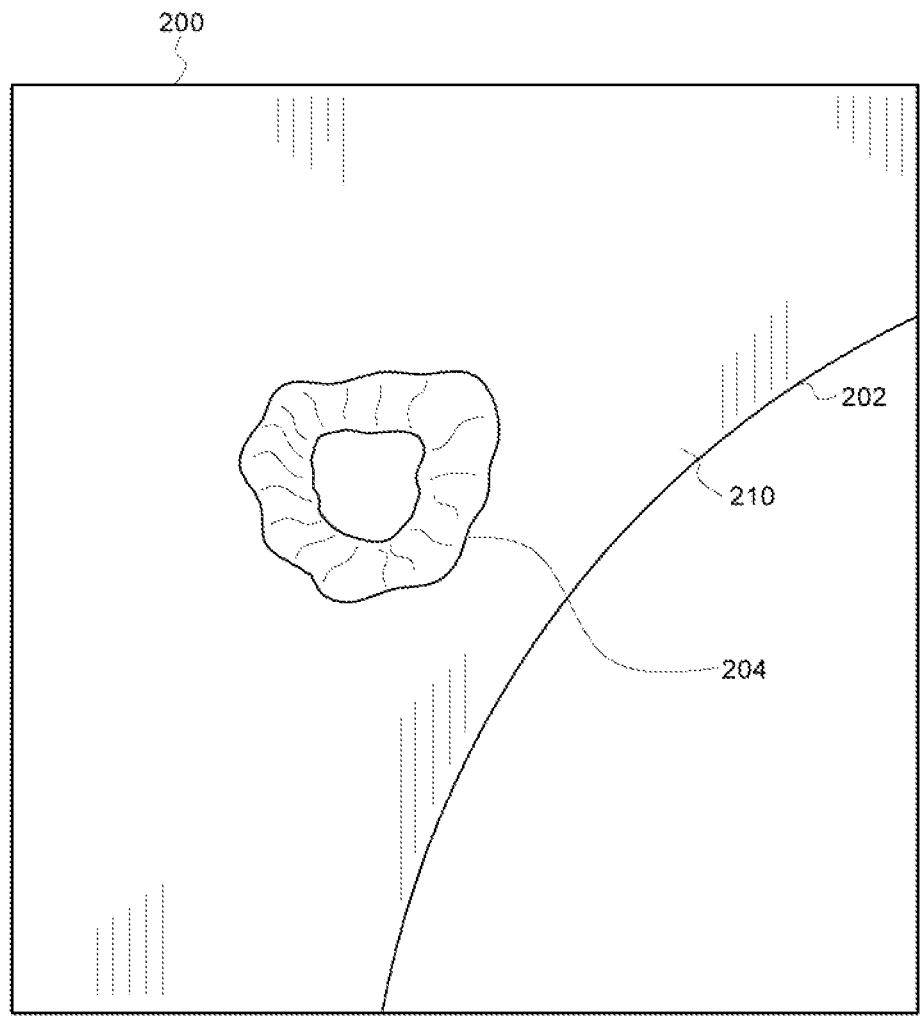
FIG. 2 is an exemplary image obtained by the video inspection device of the surface of a viewed object having an anomaly in an exemplary embodiment of the invention.

FIG. 2 is an exemplary image 200 obtained by the video inspection device 100 of the surface 210 of a viewed object 202 having an anomaly 204 in an exemplary embodiment of the invention. In this example, the anomaly 204 is shown as a dent, where material has been removed from the surface 210 of the viewed object 202 in the anomaly 204 by damage or wear. It will be understood that the anomaly 204 shown in this exemplary embodiment is just an example and that the inventive method applies to other types of irregularities (e.g., cracks, corrosion pitting, coating loss, surface deposits, etc.). Once the image 200 is obtained, and the anomaly 204 is identified, the image 200 can be used to determine the dimensions of the anomaly 204 (e.g., height or depth, length, width, area, volume, point to line, profile slice, etc.). In one embodiment, the image 200 used can be a two-dimensional image 200 of the surface 210 of the viewed object 202, including the anomaly 204.

Figure 3:
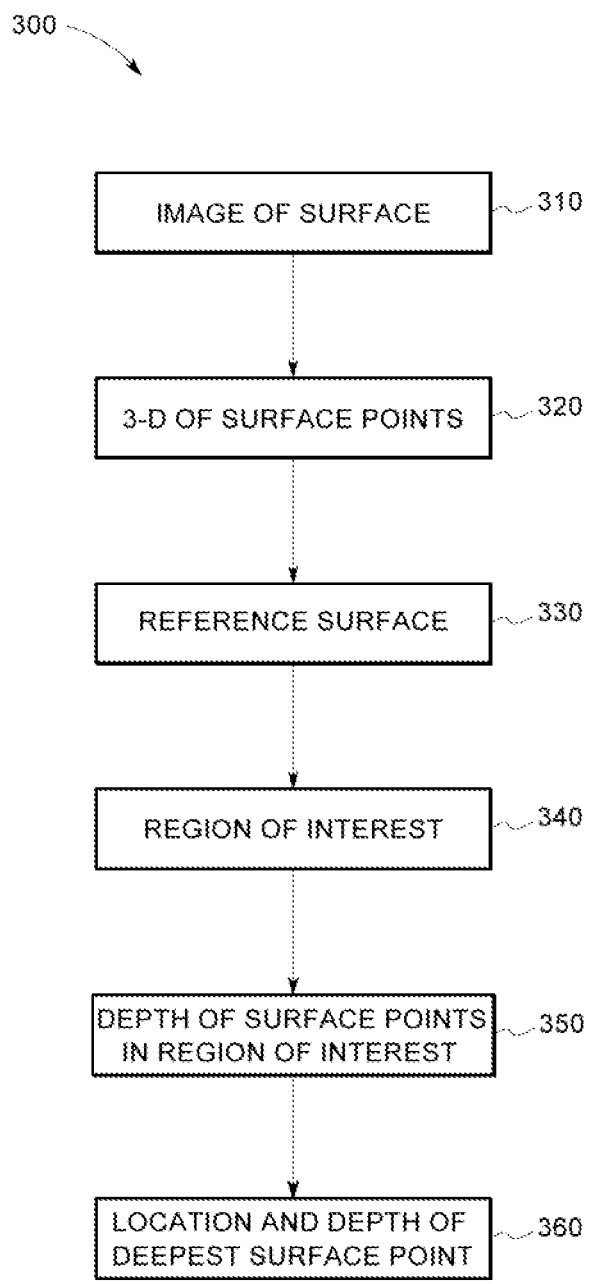
FIG. 3 is a flow diagram of an exemplary method and device for automatically identifying the deepest point on the surface of an anomaly on a viewed object shown in the image of FIG. 2 in an exemplary embodiment of the invention.

FIG. 3 is a flow diagram of an exemplary method 300 for automatically identifying the deepest point on the surface 210 of an anomaly 204 on a viewed object 202 shown in the image 200 of FIG. 2 in an exemplary embodiment of the invention. It will be understood that the steps described in the flow diagram of FIG. 3 can be performed in a different order than shown in the flow diagram and that not all of the steps are required for certain embodiments.

At step 310 of the exemplary method 300 (FIG. 3) and as shown in FIG. 2, the user can use the video inspection device 100 (e.g., the imager 124) to obtain at least one image 200 of the surface 210 of a viewed object 202 having an anomaly 204 and display it on a video monitor (e.g., an integral display 170 or external monitor 172).

At step 320 of the exemplary method 300 (FIG. 3), the video inspection device 100 (e.g., the CPU 150) can determine the three-dimensional coordinates (e.g., (x, y, z)) of a plurality of surface points on the surface 210 of the viewed object 202, including surface points of the anomaly 204. In one embodiment, the video inspection device can generate three-dimensional data from the image 200 in order to determine the three-dimensional coordinates. Several different existing techniques can be used to provide the three-dimensional coordinates of the surface points in the image 200 (FIG. 2) of the surface 210 (e.g., stereo, scanning systems, stereo triangulation, structured light methods such as phase shift analysis, phase shift moiré, laser dot projection, etc.).

Most such techniques comprise the use of calibration data, which, among other things, includes optical characteristic data that is used to reduce errors in the three-dimensional coordinates that would otherwise be induced by optical distortions. With some techniques, the three-dimensional coordinates may be determined using one or more images captured in close time proximity that may include projected patterns and the like. It is to be understood that references to three-dimensional coordinates determined using image 200 may also comprise three-dimensional coordinates determined using one or a plurality of images 200 of the surface 210 captured in close time proximity, and that the image 200 displayed to the user during the described operations may or may not actually be used in the determination of the three-dimensional coordinates.

Figure 4:
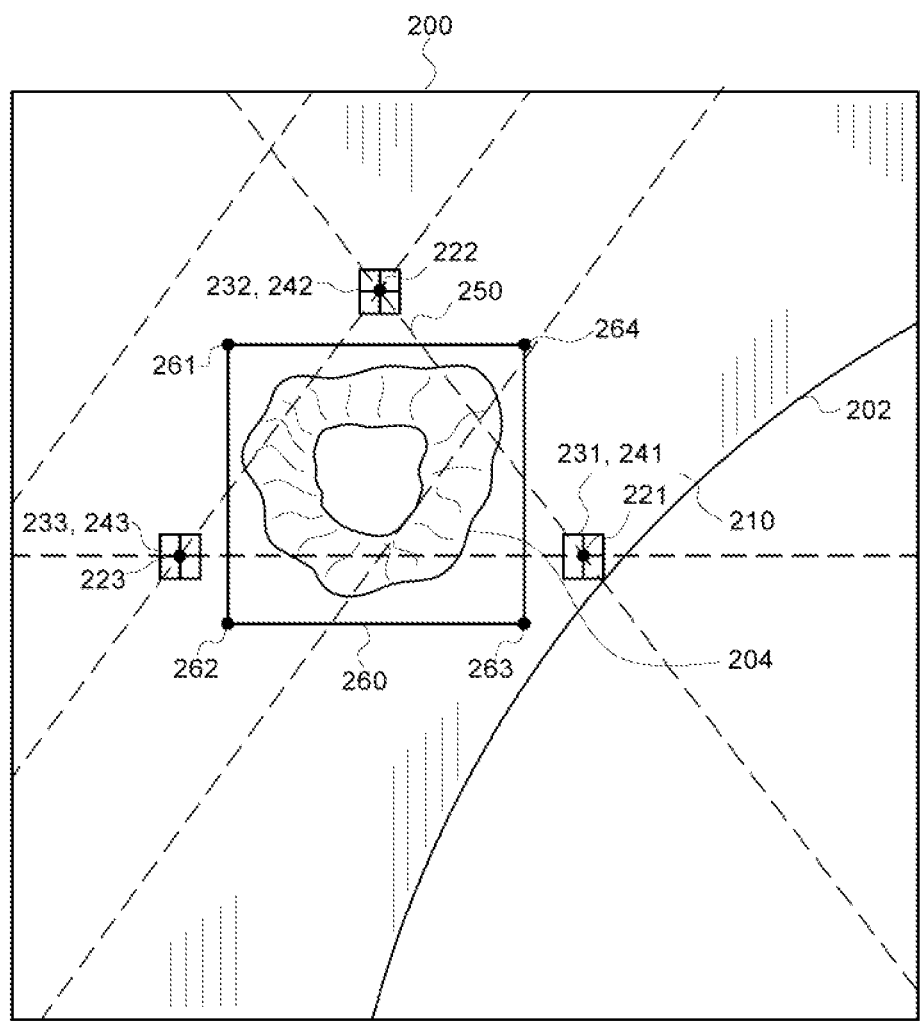
FIG. 4 illustrates an exemplary reference surface determined by the video inspection device.

At step 330 of the exemplary method 300 (FIG. 3), and as shown in FIG. 4, the video inspection device 100 (e.g., the CPU 150) can determine a reference surface 250. In some embodiments, the reference surface 250 can be flat, while in other embodiments the reference surface 250 can be curved. Similarly, in one embodiment, the reference surface 250 can be in the form of a plane, while in other embodiments, the reference surface 250 can be in the form of a different shape (e.g., cylinder, sphere, etc.). For example, a user can use the joystick 180 (or other pointing device (e.g., mouse, touch screen)) of the video inspection device 100 to select one or more reference surface points on the surface 210 of the viewed object 202 proximate to the anomaly 204 to determine a reference surface.

In one embodiment and as shown in FIG. 4, a total of three reference surface points 221, 222, 223 are selected on the surface 210 of the viewed object 202 proximate to the anomaly 204 to conduct a depth measurement of the anomaly 204, with the three reference surface points 221, 222, 223 selected on the surface 210 proximate to the anomaly 204. In one embodiment, the plurality of reference surface points 221, 222, 223 on the surface 210 of the viewed object 202 can be selected by placing reference surface cursors 231, 232, 233 (or other pointing devices) on pixels 241, 242, 243 of the image 200 corresponding to the plurality of reference surface points 221, 222, 223 on the surface 210. In the exemplary depth measurement, the video inspection device 100 (e.g., the CPU 150) can determine the three-dimensional coordinates of each of the plurality of reference surface points 221, 222, 223.

The three-dimensional coordinates of three or more surface points proximate to one or more of the three reference surface points 221, 222, 223 selected on the surface 210 proximate to the anomaly 204 can be used to determine a reference surface 250 (e.g., a plane). In one embodiment, the video inspection device 100 (e.g., the CPU 150) can perform a curve fitting of the three-dimensional coordinates of the three reference surface points 221, 222, 223 to determine an equation for the reference surface 250 (e.g., for a plane) having the following form:

$$k_{0RS} + k_{1RS1} \cdot x_{iRS} + k_{2RS} \cdot y_{iRS1} = z_{iRS} \quad (1)$$

where ($x_{iRS}$, $y_{iRS}$, $z_{iRS}$) are coordinates of any three dimensional point on the defined reference surface 250 and $k_{0RS}$, $k_{1RS}$, and $k_{2RS}$ are coefficients obtained by a curve fitting of the three-dimensional coordinates.

It should be noted that a plurality of reference surface points (i.e., at least as many points as the number of k coefficients) are used to perform the curve fitting. The curve fitting finds the k coefficients that give the best fit to the points used (e.g., least squares approach). The k coefficients then define the plane or other reference surface 250 that approximates the three-dimensional points used. However, if more points are used in the curve fitting than the number of k coefficients, when you insert the x and y coordinates of the points used into the plane equation (1), the z results will generally not exactly match the z coordinates of the points due to noise and any deviation from a plane that may actually exist. Thus, the $x_{iRS1}$ and $y_{iRS1}$ can be any arbitrary values, and the resulting $z_{iRS}$ tells you the z of the defined plane at $x_{iRS}$, $y_{iRS}$. Accordingly, coordinates shown in these equations can be for arbitrary points exactly on the defined surface, not necessarily the points used in the fitting to determine the k coefficients.

In other embodiments, there are only one or two reference surface points selected, prohibiting the use of curve fitting based only on the three-dimensional coordinates of those reference surface points since three points are needed to determine $k_{0RS}$, $k_{1RS}$, and $k_{2RS}$. In that case, the video inspection device 100 (e.g., the CPU 150) can identify a plurality of pixels proximate to each of the pixels of the image corresponding to a plurality of points on the surface 210 proximate to the reference surface point(s), and determine the three-dimensional coordinates of the proximate point(s), enabling curve fitting to determine a reference surface 250.

While the exemplary reference surface 250 has been described as being determined based on reference surface points 221, 222, 223 selected by reference surface cursors 231, 232, 233, in other embodiments, the reference surface 250 can be formed by using a pointing device to place a reference surface shape 260 (e.g., circle, square, rectangle, triangle, etc.) proximate to anomaly 204 and using the reference surface points 261, 262, 263, 264 of the shape 260 to determine the reference surface 250. It will be understood that the reference surface points 261, 262, 263, 264 of the shape 260 can be points selected by the pointing device or be other points on or proximate to the perimeter of the shape that can be sized to enclose the anomaly 204.

Figure 5:
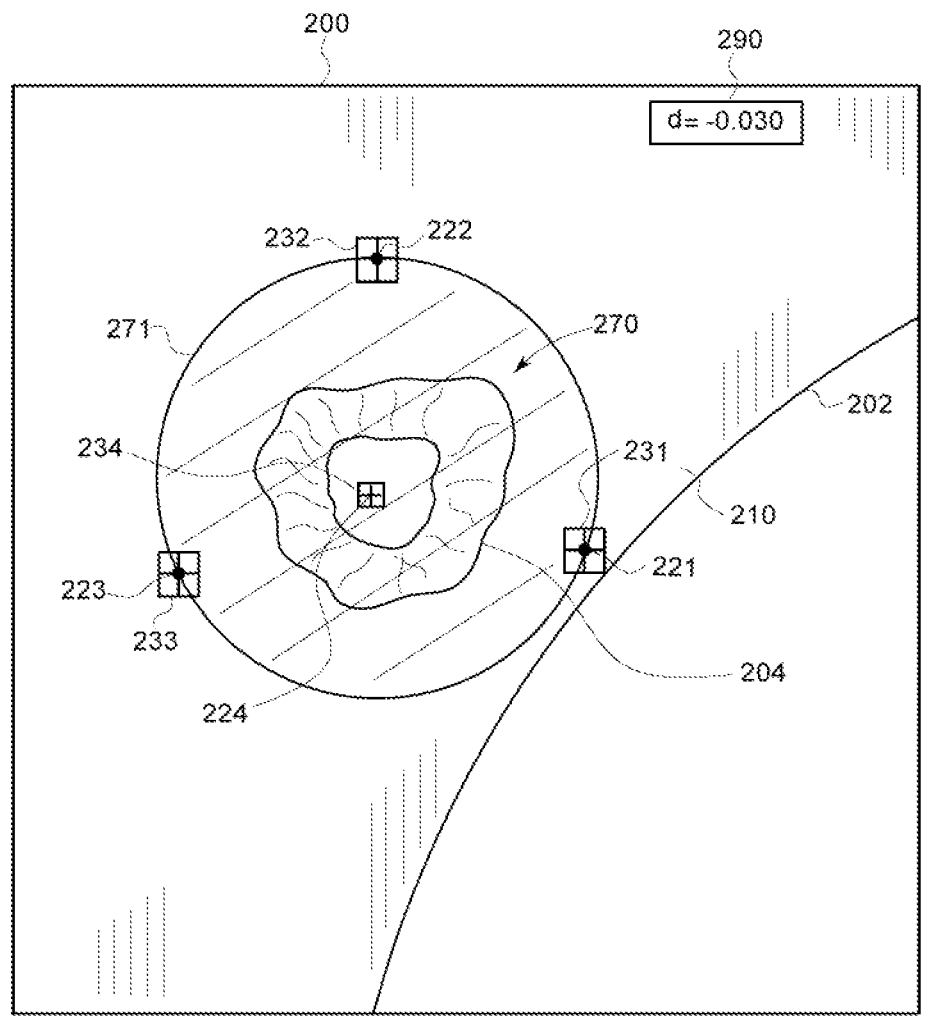
FIG. 5 illustrates an exemplary region of interest determined by the video inspection device.

At step 340 of the exemplary method 300 (FIG. 3), and as shown in FIG. 5, the video inspection device 100 (e.g., the CPU 150) determines a region of interest 270 proximate to the anomaly 204 based on the reference surface points of the reference surface 250. The region of interest 270 includes a plurality of surface points of the anomaly 204. In one embodiment, a region of interest 270 is formed by forming a region of interest shape 271 (e.g., a circle) based on two or more of the reference surface points 221, 222, 223. In another embodiment, the region of interest 270 can be determined by forming a cylinder perpendicular to the reference surface 260 and passing it through or proximate to two or more of the reference surface points 221, 222, 223. Referring again to FIG. 4, a region of interest could be formed within the reference surface shape 260 and reference surface points 261, 262, 263, 264.

Figure 6:
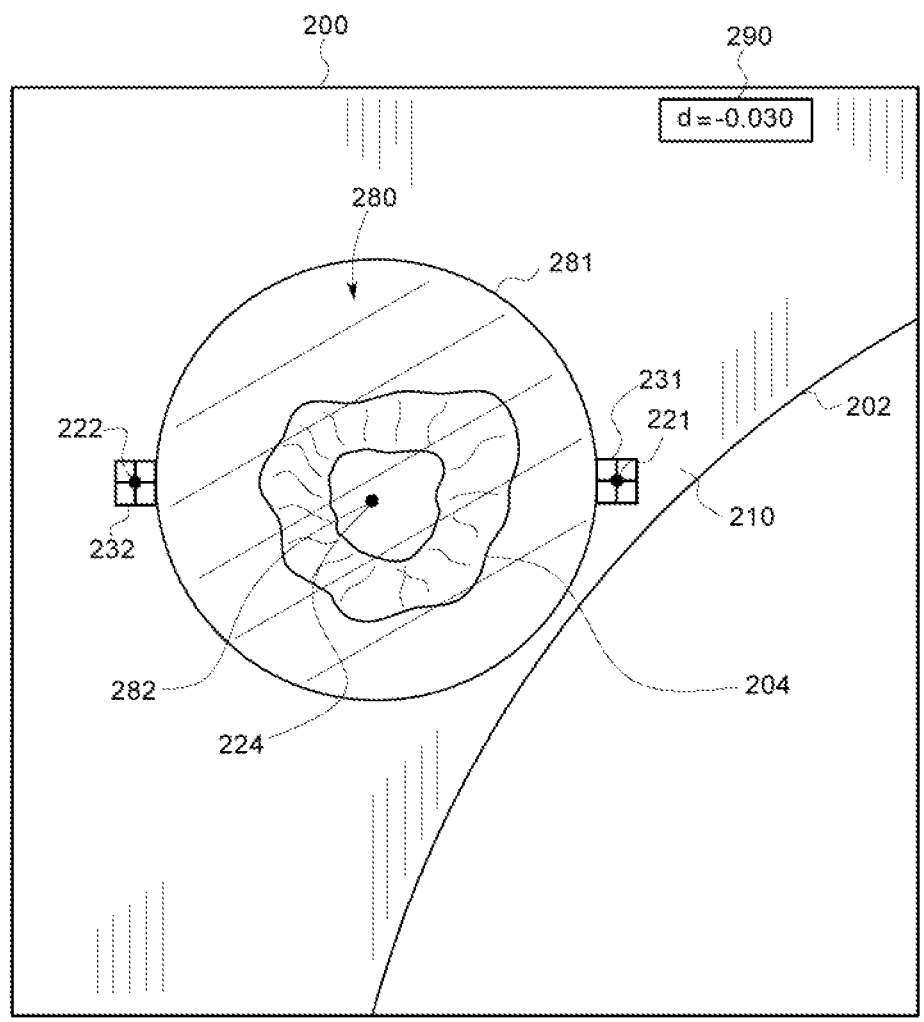
FIG. 6 illustrates another exemplary region of interest determined by the video inspection device.

Although the exemplary region of interest shape 271 in FIG. 5 is formed by passing through the reference surface points 221, 222, 223, in another embodiment, a smaller diameter reference surface shape can be formed by passing only proximate to the reference surface points. For example, as shown in FIG. 6, a region of interest 280 is formed by passing a region of interest shape 281 (e.g., a circle) proximate to two of the reference surface points 221, 222, where the diameter of the circle 281 is smaller than the distance between the two reference surface points 221, 222. It will be understood that region of interest shapes 271, 281 and the regions of interest 270, 280 may or may not be displayed on the image 200.

After the region of interest 270, 280 is determined, at step 350 of the exemplary method 300 (FIG. 3), the video inspection device 100 (e.g., the CPU 150) determines the distance (i.e., depth) from each of the plurality of surface points in the region of interest to the reference surface 250. In one embodiment, the video inspection device 100 (e.g., the CPU 150) determines the distance of a line extending between the reference surface 250 and each of the plurality of surface points in the region of interest 270, 280, wherein the line perpendicularly intersects the reference surface 250.

At step 360 of the exemplary method 300 (FIG. 3), the video inspection device determines the location of the deepest surface point 224 in the region of interest 270, 280 by determining the surface point that is furthest from the reference surface 250 (e.g., selecting the surface point with the longest line extending to the reference surface 250). It will be understood that, as used herein, the "deepest point" or "deepest surface point" can be a furthest point that is recessed relative to the reference surface 250 or a furthest point that is protruding from the references surface 250. The video inspection device 100 can identify the deepest surface point 224 in the region of interest 270, 280 on the image by displaying, e.g., a cursor 234 (FIG. 5) or other graphic identifier 282 (FIG. 6) on the deepest surface point 224. In addition and as shown in FIGS. 5 and 6, the video inspection device 100 can display the depth 290 (in inches or millimeters) of the deepest surface point 224 in the region of interest 270, 280 on the image 200 (i.e., the length of the perpendicular line extending from the deepest surface point 224 to the reference surface 250. By automatically displaying the cursor 234 or other graphic identifier 282 (FIG. 6) at the deepest surface point 224 in the region of interest 270, 280, the video inspection device 100 reduces the time required to perform the depth measurement and improves the accuracy of the depth measurement since the user does not need to manually identify the deepest surface point 224 in the anomaly 204.

Once the cursor 234 has been displayed at the deepest surface point 224 in the region of interest 270, 280, the user can select that point to take and save a depth measurement. The user can also move the cursor 234 within the region of interest 270, 280 to determine the depth of other surface points in the region of interest 270, 280. In one embodiment, the video inspection device 100 (e.g., CPU 150) can monitor the movement of the cursor 234 and detect when the cursor 234 has stopped moving. When the cursor 234 stops moving for a predetermined amount of time (e.g., 1 second), the video inspection device 100 (e.g., the CPU 150) can determine the deepest surface point proximate to the cursor 234 (e.g., a predetermined circle centered around the cursor 234) and automatically move the cursor 234 to that position.

Figure 7:
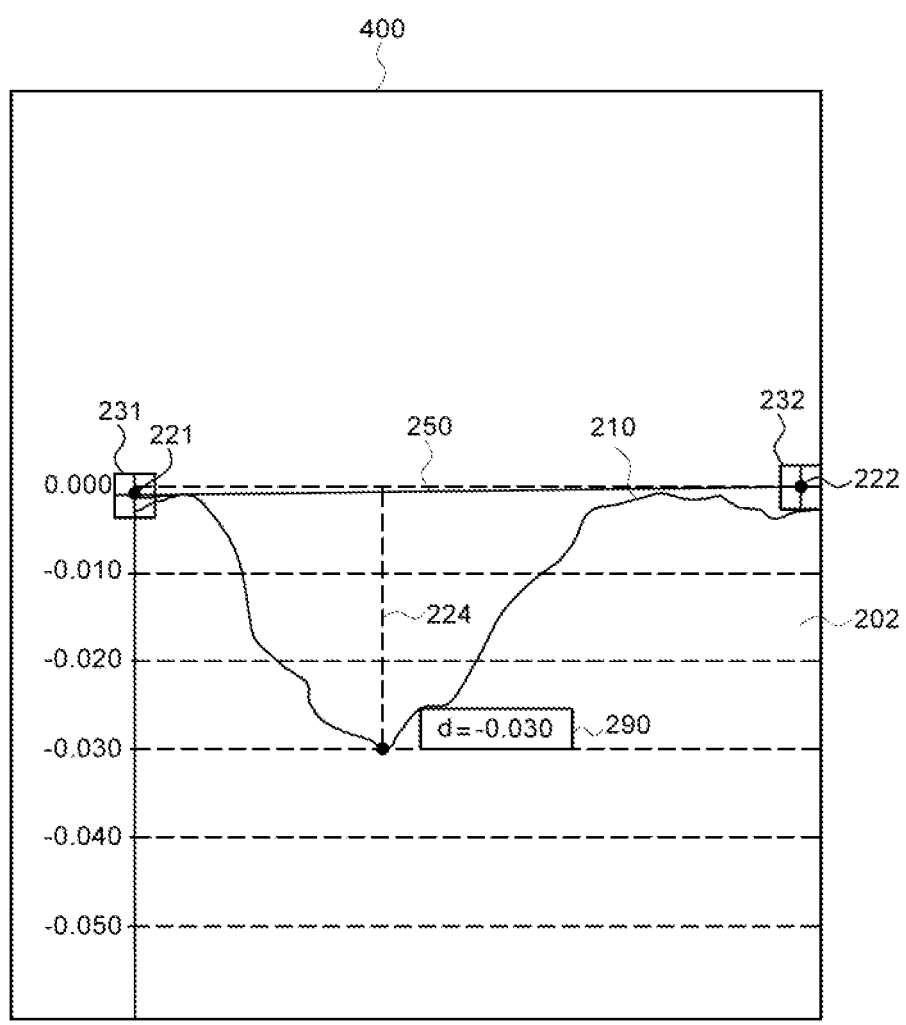
FIG. 7 is a graphical representation of an exemplary profile of the surface of the viewed object shown in the image of FIG. 1 in an exemplary embodiment of the invention.

FIG. 7 is a graphical representation of an exemplary profile 400 of the surface 210 of the viewed object 202 shown in the image 200 of FIG. 1. In this exemplary profile 400, the reference surface 250 is shown extending between two reference surface points 221, 222 and their respective reference surface cursors 231, 232. The location and depth 290 of the deepest surface point 224 in the region of interest is also shown in the graphical representation. In another embodiment, a point cloud view can also be used to show the deepest surface point 224.

In view of the foregoing, embodiments of the invention automatically determine the depth of an anomaly on a surface. A technical effect is to reduce the time required to perform the depth measurement and to improve the accuracy of the depth measurement since the user does not need to manually identify the deepest point.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of automatically identifying a deepest point on a surface of an anomaly on a surface of a viewed object, the method comprising the steps of:
    obtaining an image of the surface of the viewed object with an imager;
    displaying on a monitor an image of the viewed object;
    determining the three-dimensional coordinates of a plurality of points on the surface of the viewed object using a central processor unit;
    determining a reference surface using the central processor unit;
    determining a region of interest that includes a plurality of points on the surface of the anomaly using the central processor unit;
    determining a depth for each of the plurality of points on the surface of the anomaly in the region of interest using the central processor unit;
    determining the point on the surface of the anomaly in the region of interest having the greatest depth as the deepest point on the surface of the anomaly using the central processor unit;

displaying on the monitor a graphical indicator at the location of the deepest point on the surface of the anomaly on the image of the surface of the anomaly;

monitoring the movement of the graphical indicator in the region of interest using the central processor unit;

detecting whether the graphical indicator has stopped moving using the central processor unit;

determining a depth for each of a plurality of points on the surface of the anomaly proximate to the graphical indicator using the central processor unit, identifying the point on the surface of the anomaly proximate to the graphical indicator having the greatest depth as the deepest point on the surface of the anomaly proximate to the graphical indicator using the central processor unit; and moving the graphical indicator to the deepest point on the surface of the anomaly proximate to the graphical indicator.

2. The method of claim 1, wherein the graphical indicator is a cursor.

3. The method of claim 1, further comprising the step of displaying on the monitor the depth of the deepest point on the surface of the anomaly.

4. The method of claim 1, wherein the image is a two-dimensional image.

5. The method of claim 1, wherein the step of determining a reference surface comprises:
selecting a plurality of reference surface points on the surface of the viewed object proximate to the anomaly using a pointing device; and
performing a curve fitting of the three-dimensional coordinates of the plurality of reference surface points.

6. The method of claim 1, wherein the step of determining a reference surface comprises:
placing a reference surface shape proximate to the anomaly using a pointing device, wherein the reference surface shape comprises a plurality of reference surface points on the surface of the viewed object; and
performing a curve fitting of the three-dimensional coordinates of the plurality of reference surface points.

7. The method of claim 1, wherein the reference surface is one of a plane, cylinder, and a sphere.

8. The method of claim 5, wherein the step of determining a region of interest that includes a plurality of points on the surface of the anomaly comprises forming a region of interest shape proximate to the anomaly based on the reference surface points on the surface of the viewed object.

9. The method of claim 8, wherein the region of interest shape is formed by passing a shape through or proximate to the reference surface points.

10. The method of claim 8, wherein the region of interest shape is one of a circle, square, rectangle, triangle, and cylinder.

11. The method of claim 1, wherein the step of determining a depth for each of the plurality of points on the surface of the anomaly in the region of interest comprises determining the distance of a line extending between the reference surface and each point, wherein the line perpendicularly intersects the reference surface.

12. The method of claim 1, wherein the step of determining the point on the surface of the anomaly in the region of interest having the greatest depth as the deepest point on the surface of the anomaly comprises selecting the point with the longest line extending between the reference surface and each of the plurality of points on the surface of the anomaly in the region of interest.

13. The method of claim 1, wherein the deepest point on the surface of the anomaly in the region of interest is recessed relative to the reference surface.

14. The method of claim 1, wherein the deepest point on the surface of the anomaly in the region of interest is protruding relative to the reference surface.

15. A device for automatically identifying a deepest point on a surface of an anomaly on a surface of a viewed object, the device comprising:
an imager for obtaining an image of the surface of the viewed object;
a monitor for displaying an image of the viewed object; and
a central processor unit for
determining the three-dimensional coordinates of a plurality of points on the surface of the viewed object,
determining a reference surface,
determining a region of interest that includes a plurality of points on the surface of the anomaly,
determining a depth for each of the plurality of points on the surface of the anomaly in the region of interest,
determining the point on the surface of the anomaly in the region of interest having the greatest depth as the deepest point on the surface of the anomaly and displaying on the monitor a graphical indicator at the location of the deepest point on the surface of the anomaly on the image of the surface of the anomaly;
monitoring the movement of the graphical indicator in the region of interest;
detecting whether the graphical indicator has stopped moving;
determining a depth for each of a plurality of points on the surface of the anomaly proximate to the graphical indicator, and
identifying the point on the surface of the anomaly proximate to the graphical indicator having the greatest depth as the deepest point on the surface of the anomaly proximate to the graphical indicator.

16. The device of claim 15, further comprising a pointing device for selecting a plurality of reference surface points on the surface of the viewed object proximate to the anomaly, wherein the plurality of reference surface points are used for determining the reference surface by performing a curve fitting of the three-dimensional coordinates of the plurality of reference surface points.

17. The device of claim 15, further comprising a pointing device for placing a reference surface shape proximate to the anomaly, wherein the reference surface shape comprises a plurality of reference surface points on the surface of the viewed object, and wherein the plurality of reference surface points are used for determining the reference surface by performing a curve fitting of the three-dimensional coordinates of the plurality of reference surface points.

18. The device of claim 15, wherein the graphical indicator is a cursor.

* * * * *